(12) United States Patent
Geckeler et al.

(10) Patent No.: US 7,122,664 B2
(45) Date of Patent: Oct. 17, 2006

(54) CUCURBITURIL-FULLERENE COMPLEX

(75) Inventors: Kurt E. Geckeler, Kwangju (KR); Friederike Constabel, Kwangju (KR)

(73) Assignee: Kwangju Institute of Science and Technology, Kwangju (KR)

( * ) Notice: Subject to any disclaimer, the term of this patent is extended or adjusted under 35 U.S.C. 154(b) by 490 days.

(21) Appl. No.: 10/667,221

(22) Filed: Sep. 17, 2003

(65) Prior Publication Data
US 2004/0167328 A1  Aug. 26, 2004

(30) Foreign Application Priority Data
Feb. 25, 2003  (KR) .................. 10-2003-0011583

(51) Int. Cl.
*C07D 245/00*  (2006.01)

(52) U.S. Cl. ................................................ 540/472
(58) Field of Classification Search ................. 540/472
See application file for complete search history.

(56) References Cited
OTHER PUBLICATIONS

Jeon et al., J. Am. Chem. Soc. 1996, 118, 9790-9791.*

* cited by examiner

*Primary Examiner*—Bruck Kifle
(74) *Attorney, Agent, or Firm*—Harness, Dickey & Pierce, P.L.C.

(57) ABSTRACT

The present invention relates to a complex composed of cucurbituril and fullerene and a method for manufacturing the complex on a solid-phase.

A complex in accordance with the present invention can be usefully used as a medicine delivery means in the field of pharmaceutics.

6 Claims, 2 Drawing Sheets

CB[7]

though graphite-made or chrome alloy-made mixing crusher can be used. The molar ratio between the solid-phase cucurbituril and fullerene is ranged from 1:2 to 2:1, preferably 2:1.

CUCURBITURIL-FULLERENE COMPLEX

BACKGROUND OF THE INVENTION

1. Field of the Invention

The present invention relates to a complex composed of cucurbituril and fullerene and a method for manufacturing the complex on a solid-phase.

2. Description of the Related Art

Cucurbituril contains hard cavities, and thus it can be properly used as a host for small organic compounds. In fact, an 1:1 complex or an 1:2 complex of cucurbit[6]uril (or cucurbit[7]uril) and a guest material has been introduced, and concretely a complex of cucurbit[7]uril and 4,4'-bipyridinium-dication, produced in an aqueous solution containing alkaline-metal salt, has been reported (Mock, W. L. and Shih, N. -Y., J. Org. Chem. 1986, 51, 4440; Ong, W. et al., Org. Lett. 2002 4, 1791; and Kim, H. -J. et al., PNAS 2002, 99, 5007). Different from cyclodextrin, a carbonyl group, located at the entrance of a cavity of cucurbituril, can be coupled with polarizable molecules and ions by ion-bipolar reaction and/or hydrogen bonding (Mock, W. L., Top. Curr. Chem. 1995, 175, 1; and Cintas, P. J., J. Inclusion Phenom. Mol. Recognit. Chem. 1994, 17, 205). These complexes are generally produced in a solution, or produced by two-phase reaction between solid-phase cucurbituril and liquid- or gas-phase guest molecules (Mock, W. L. and Shih, N. -Y., J. Org. Chem. 1986, 51, 4440; and Buschmann, H. -J. et al., European Water Pollution Control 1996, 6, 21).

Cucurbit[6,7]uril is a very desirable composition unit of an acceptor-supramolecule compound composition (Jeon, Y. -M. et al., J. Am. Chem. Soc. 1996, 118, 9790; and Zhao, J. et al., Angew. Chem. Int. Ed. 2001, 40, 4233), however, its characteristics and applicability have not been studied very much. Up to the present, guest materials that have been used for manufacturing a cucurbituril-containing complex are limited to iodine (Saenger, W., Angew. Chem. 1980, 92, 343), dyes for water-purification (Buschmann, H. -J. et al., European Water Pollution Control, 1996, 6, 21), and alkyl- and aryl-ammonium ions (Mock, W. L.; Shih, N. -Y.; J. Org. Chem. 1986, 51, 4440). And, it has not been reported about a complex of cucurbituril and nonpolar guest material.

In addition, fullerene has a very high reactivity to a free radical (Krusic, P. J. et al., Science 1991, 254 1183; Geckeler, K. E. and Arsalani, N., Fullerene Sci. Technol. 1996, 4, 897; and Ford, W. T. et al., Macromolecules 1997, 30, 6422) and is able to cut DNA with light being existed, and thus it has very high applicability for bio-medicines. Consequently, it has been broadly researched on a host-guest material chemistry of [60]fullerene. It has been reported that various molecules such as β- and γ-cyclodextrin' (Murthy, C. N. and Geckeler, K. E., Chem. Commun. 2001, 1194; Murthy, C. N. and Geckeler, K. E., Full., Nanotubes, & Carb. Nanostructures 2002, 10(2), 91; and Anderson, T. et al., Chem. Soc. Chem. Commun. 1992, 604), calix[3,5,6,8]arenes (Ikeda, A. et al., J. Am. Chem. Soc. 1999, 121, 4296; and EP0686644), and porphyrin-metal macro-ring (Tashiro, K. et al., J. Am. Chem. Soc. 1999, 121, 9477) are working as a host for [60]fullerene respectively.

SUMMARY OF THE INVENTION

The inventors of the present invention conceived the broad applicability of cucurbituril and fullerene. So, we tried to produce a complex of cucurbituril and fullerene, a nonpolar material. As a result, we developed a novel complex composition method of manufacturing a complex by solid-phase reaction that is very easy and effective.

It is an object of the present invention to provide a complex of cucurbituril and fullerene.

It is another object of the present invention to provide a method for manufacturing a complex of cucurbituril and fullerene.

To achieve the object mentioned above, the present invention provides a cucurbituril-fullerene complex in which cucurbituril and fullerene are being coupled by molecular interaction.

To achieve the another object mentioned above, the present invention provides a method for manufacturing a complex containing cucurbituril and fullerene that includes crushing a mixture of solid-phase cucurbituril and fullerene.

DETAILED DESCRIPTION OF THE EMBODIMENTS

Figure 1:
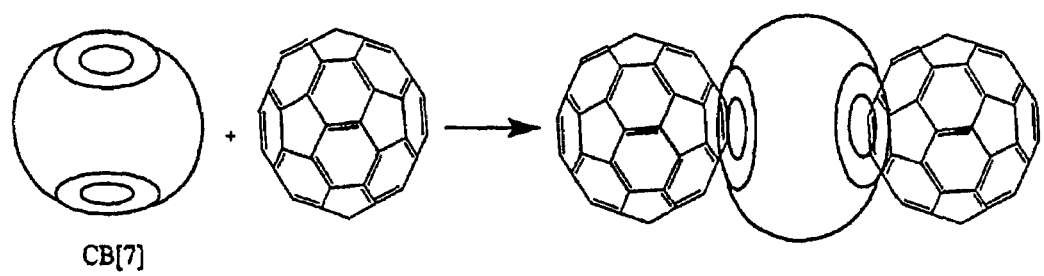
FIG. 1 is a view illustrating the coupling state of a cucurbit[7]uril-[60]fullerene complex.

Hereinafter, the present invention is described in detail.

A complex in accordance with the present invention is a supramolecular complex comprising cucurbituril and fullerene. The cucurbituril used in the present invention is not deformed and comprises cucurbit[6]uril or cucurbit[7] uril. All kinds of fullerenes fit for the cavities of said cucurbituril, such as [60]fullerene, [70]fullerene, etc., can be used in the present invention.

The fullerene used in the present invention is nonpolar material and coupled at the entrance of the cavity of cucurbituril entirely by molecular interaction, not by covalent bonding, to form a stable complex.

The molar ration of the initial compounds, Cucurbit[7]uril and C60, ranged between 1:2 and 2:1. In all cases the formation of a CUC7:F6=1:2 complex could be observed.

Fullerene, used in the present invention, has potential characteristics as a bio-medicine such as the functions of eliminating free radicals, cutting DNA, and the like. And cucurbituril is working as acceptor or absorption material of fullerene. Thus, a complex in accordance with the present invention can be used as a medicine delivery means in the field of pharmaceutics.

The complex in accordance with the present invention has a single-phase and can be obtained by solid-phase reaction. In other words, a complex in accordance with the present invention can be obtained by crushing a mixture of solid-phase cucurbituril and fullerene.

In more detail, a complex in accordance with the present invention can be obtained by mixing solid-phase fullerene and solid-phase cucurbituril with molar ratio from 1:2 to 2:1, preferably with 2:1, and crushing the mixture in a mixing crusher under the room temperature, preferably in a chrome steel mixing crusher with chrome steel crushing balls being added, with the rotation speed from 20 rpm for about 1 to 10 hours.

Hereinafter, an embodiment of the present invention is described in detail.

Here, the embodiment is only for an example of the present invention, and the present invention is not limited to the embodiment.

[Embodiment 1]—Manufacturing a Complex of Cucurbit [7]Uril and [60]Fullerene.

In a typical experiment, a complex was produced by crushing a mixture of 20.1 mg ($28\times10^{-3}$ mmol) of [60]fullerene and 16.3 mg ($14\times10^{-3}$ mmol) of cucurbit[7]uril (CB[7]) in a chrome steel mixing crusher using chrome steel crushing balls. The crushing was being carried out with the speed of 20 rpm for 1 to 10 hours. After washing-out the produced CB[7]-$C_{60}$ fullerene complex with warm water, we added 2M of NaOH to the solution to control its pH to be 12 and added 20 ml of toluene thereto to dissolve the remaining CB[7] and non-coupled [60]fullerene. After dissolving excessive initial compounds by agitation the mixture for 30 minutes, we allowed the complex to precipitate. The aqueous phase containing the insoluble complex was frozen, so that the upper organic phase could be decanted. Next, after leaving the aqueous-phase until it gets back to room temperature, we centrifuged it under 0° C. with 5000 rpm for 10 minutes, and then poured out the water carefully. After washing the complex with pure water until its pH got to be neutral, we finally evaporated the remained water and vacuum-dried the dark-brown complex to obtain the complex of the present invention (yield rate: 33%).

Figure 2:
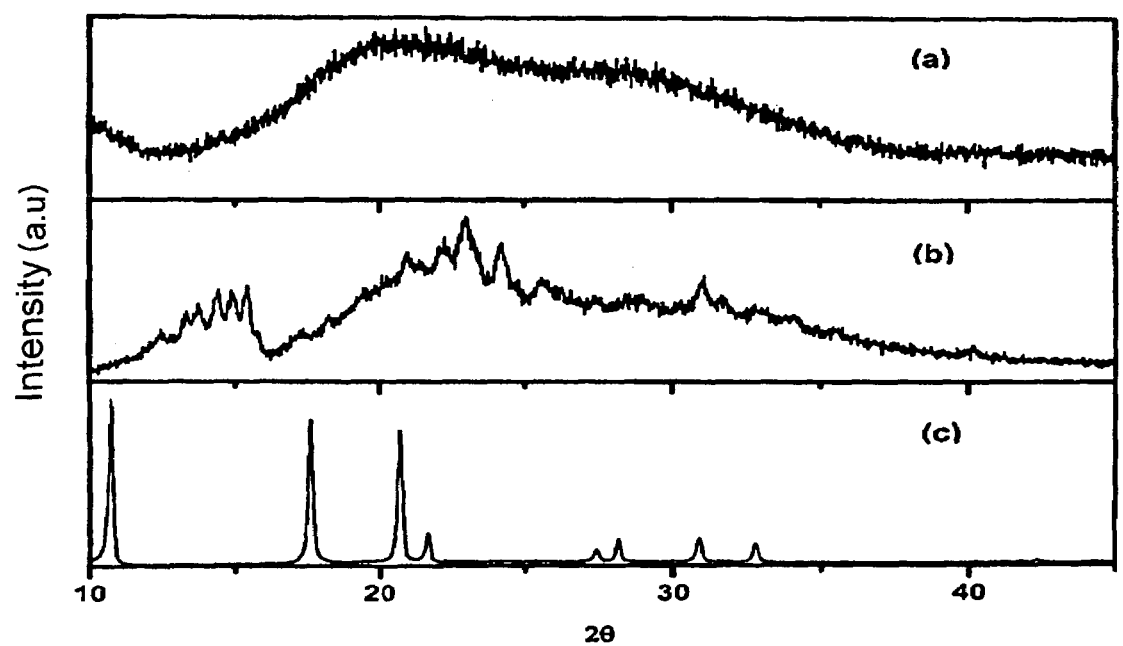
FIG. 2 is a graph showing the X-ray diffraction analysis results of (a) cucurbit[7]uril-[60]fullerene complex, (b) cucurbit[7]1uril and (c) [60]fullerene.

Referring to the X-ray diffraction analysis results shown in FIG. 2, the produced complex did not show the typical 2θ values of cucurbit[7]uril and [60]fullerene. Like the cases observed in other complexes containing [60]fullerene, it is shown that the crystal structures of initial compositors, i.e., cucurbit[7]uril and [60]fullerene, are concealed, by forming a complex, in the complex of the present invention.

Figure 3:
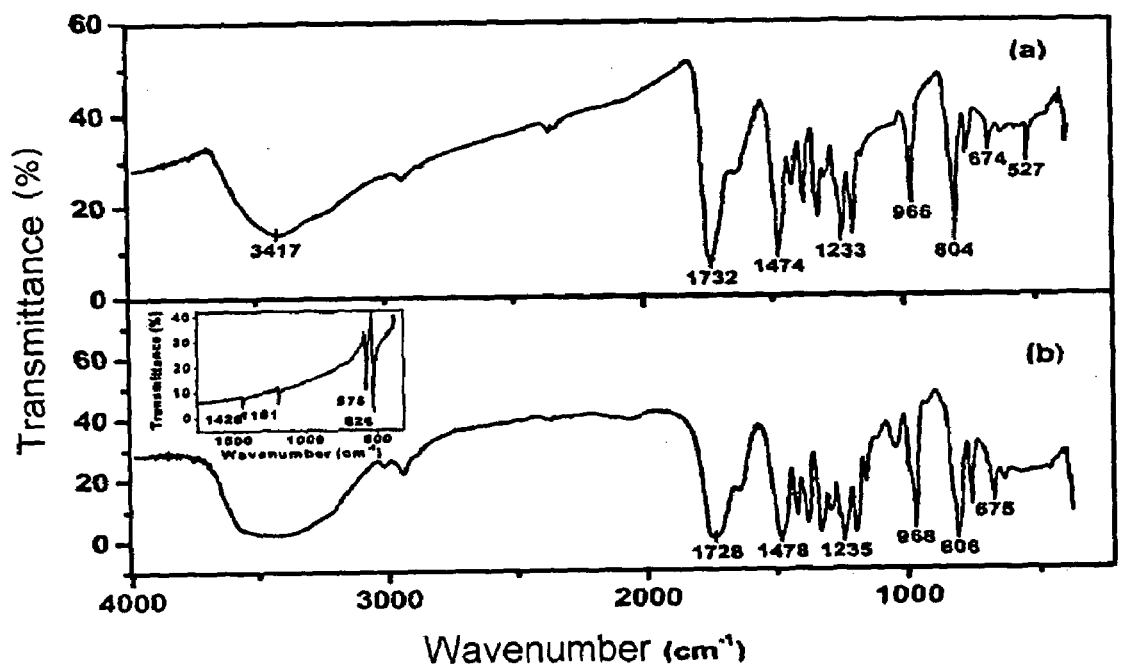
FIG. 3 is a graph showing the FT-IR spectrums of (a) cucurbit[7]uril-[60]fullerene complex, (b) cucurbit[7]uril and (c) [60]fullerene.
Figure 4:
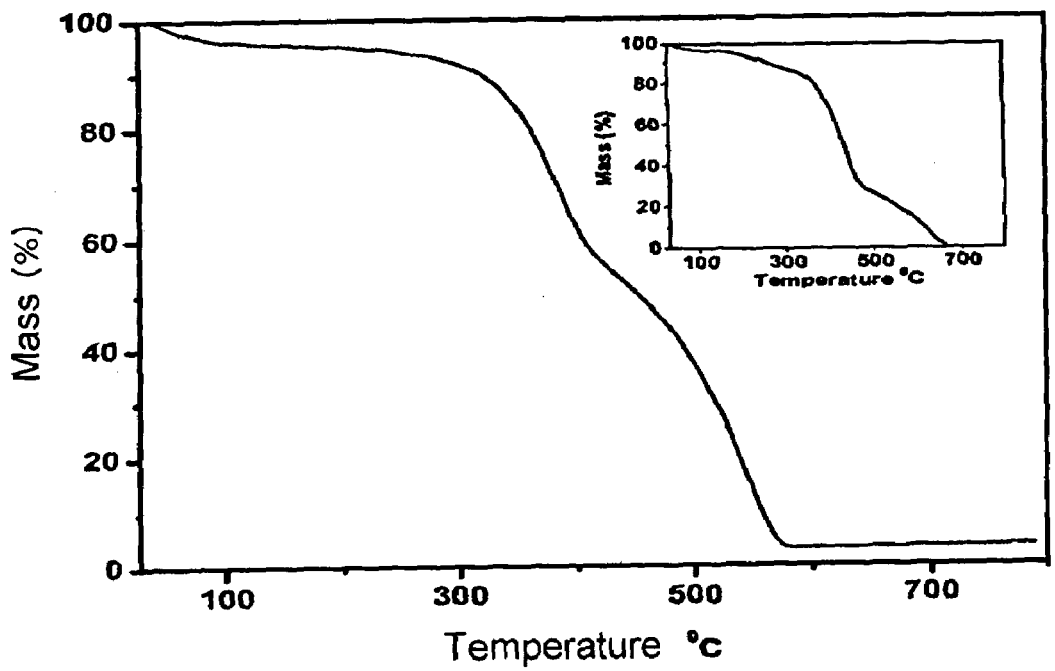
FIG. 4 is a graph showing the thermo-gravimetric analysis results of cucurbit[7]uril-[60]fullerene complex and cucurbit [7]uril.

Referring to the FT-IR spectrums shown in FIG. 3, a characteristic absorption band of cucurbit[7]uril and a typical absorption band of $C_{60}$ fullerene are shown at 527 $cm^{-1}$.

That is to say, it represents that the complex obtained in the present invention comprises cucurbit[7]uril and $C_{60}$ fullerene.

Referring to the thermo-gravimetric analysis results shown in FIG. 3, the total weight loss of the complex of cucurbit[7]uril and [60]fullerene was 40.1% at 410° C., and this represents that the weight ratio of cucurbit[7]uril and [60]fullerene in the complex is 1:2.

As mentioned thereinbefore, a complex in accordance with the present invention is a Supramolecular complex comprising fullerene having potential characteristics as a bio-medicine and cucurbituril working as absorption material or acceptor of fullerene. Since the complex in accordance with the present invention can be easily manufactured and handled, it can be usefully used as a medicine delivery means in the field of pharmaceutics.

What is claimed is:

1. A cucurbituril-fullerene complex in which cucurbituril and fullerene are coupled with each other by molecular interaction.

2. A cucurbituril-fullerene complex as claimed in claim 1, characterized in that the weight ratio of cucurbituril and fullerene is from 1:2 to 2:1.

3. A method for manufacturing a complex, comprising cucurbituril and fullerene, comprising the step of crushing a mixture of solid-phase cucurbituril and fullerene.

4. A method for manufacturing a complex as claimed in claim 3, characterized in that the molar ratio of cucurbituril and fullerene of said mixture is from 1:2 to 2:1.

5. A method for manufacturing a complex as claimed in claim 3, characterized in that said mixture is being crushed with the rotation speed form 20 rpm for about 1 to 10 hours.

6. A method for manufacturing a complex as claimed in claim 4, characterized in that said mixture is being crushed with the rotation speed form 20 rpm for about 1 to 10 hours.

* * * * *